United States Patent [19]

Bernardi et al.

[11] 3,963,760
[45] June 15, 1976

[54] SELECTIVE DEMETHYLATION OF ANTHRACYCLINE DERIVATIVES

[75] Inventors: Luigi Bernardi; Bianca Patelli, both of Milan, Italy

[73] Assignee: Societa' Farmaceutici Italia S.p.A., Milan, Italy

[22] Filed: Sept. 15, 1975

[21] Appl. No.: 613,423

[30] Foreign Application Priority Data

Sept. 20, 1974 United Kingdom............. 41015/74

[52] U.S. Cl. ............................................. 260/365
[51] Int. Cl.² ....................................... C07C 87/10
[58] Field of Search .................................. 260/365

[56] References Cited
UNITED STATES PATENTS

| | | | |
|---|---|---|---|
| 3,201,424 | 8/1965 | McCormick et al............ | 260/365 X |
| 3,636,063 | 1/1972 | McCormick et al............ | 260/365 |
| 3,665,018 | 5/1972 | Jolles............................. | 260/365 |

*Primary Examiner*—Paul F. Shaver
*Attorney, Agent, or Firm*—Stevens, Davis, Miller & Mosher

[57] ABSTRACT

Anthracycline derivatives of the formula

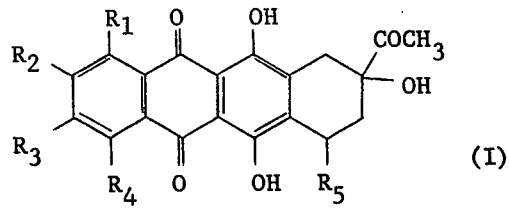

(I)

wherein $R_1$, $R_2$, $R_3$ and $R_4$ are independently selected from the group consisting of hydrogen, chlorine, bromine and methoxy, with the proviso that at least one of the substituents is methoxy, and wherein $R_5$ is selected from the group consisting of hydrogen, OH OR and OCOR; R being an alkyl group of 1 to 4 carbon atoms are prepared, in a single step, by selectively demethylating a compound of the formula:

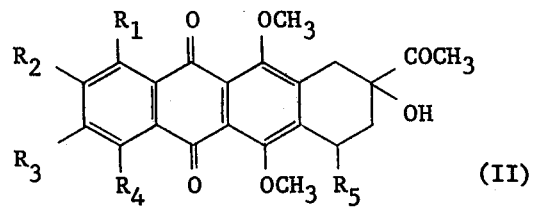

(II)

wherein $R_1$, $R_2$, $R_3$, $R_4$ and $R_5$ are as defined above by treating same with an aluminum halide in the presence of a suitable solvent at a temperature of 0° to 50°C.

4 Claims, No Drawings

SELECTIVE DEMETHYLATION OF ANTHRACYCLINE DERIVATIVES

BACKGROUND OF THE INVENTION

1. Field of the Invention

The present invention relates to anthracycline derivatives, and more particularly, to processes for the selective demethylation of anthracycline derivatives.

2. The Prior Art

The anthracyclinones of the formula:

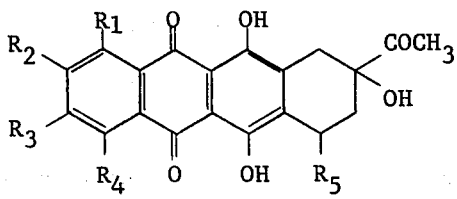

wherein $R_1$, $R_2$, $R_3$ and $R_4$ are independently selected from the group consisting of hydrogen, chlorine, bromine and methoxy, with the proviso that at least one of the substituents is methoxy, and wherein $R_5$ is selected from the group consisting of hydrogen, OH, OR and OCOR, in which R is an alkyl group containing 1 to 4 carbon atoms, are intermediates for the production of known useful antibiotics and anti-tumor agents, such as daunomycin, adriamycin and analogues thereof. For example, compounds of formula (I) can be converted to daunomycin, adriamycin, etc., by the methods described in co-pending applications Ser. Nos. 560,104 and 560,105 as well as in U.S. Pat. No. 3,803,124, all owned by the unrecorded assignee hereof.

Heretofore, compounds of formula (I) have been obtained in only very low yield, through a 4-step procedure, starting from a compound of the formula:

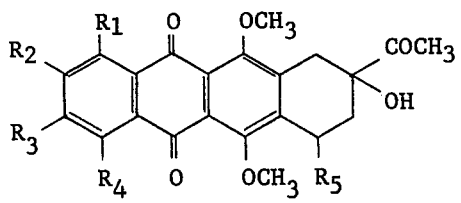

wherein $R_1$, $R_2$, $R_3$, $R_4$ and $R_5$ are as defined above. For example the compound of formula (I), wherein $R_1=R_2=R_3=H$ and $R_4=R_5=OCH_3$, has been obtained (C. M. Wong et al, Canad. J. Chem., 51, 466, 1973) from a compound of formula (II), wherein $R_1=R_2=R_3=H$ and $R_4=R_5=OCH_3$, in only 10% yield according to the following reaction sequence:

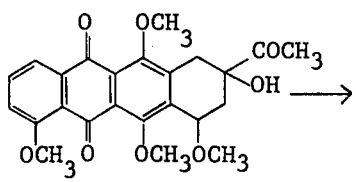

SUMMARY OF THE INVENTION

According to the invention, it has now been found that selective demethylation of compounds of the formula (II) can be achieved by treating such compounds with an aluminum halide, such as aluminum chloride or bromide in a homogeneous solution in chlorobenzene, bromobenzene or nitrobenzene, preferably, nitrobenzene, to produce compounds of the formula (I) in high yield and in a single step. The amount of aluminum halide used is not critical and can be from 1 to 20 moles per mole of compound of formula (II), but the best results are obtained with 4–8 moles of aluminum halide. The temperature at which the reaction is conducted can be varied from 0° to 50°C., but the best results are obtained at temperatures of 20°C. or less. Another important advantage of the procedure of the invention is the possibility, owing to the mild conditions employed therein, of using optically active intermediates without any loss of optical activity; thus the separation of optical isomers can be performed, with advantage, at an earlier stage of the synthetic sequence.

DESCRIPTION OF THE PREFERRED EMBODIMENTS

The following example illustrates the invention without limiting it.

EXAMPLE

7-O-Methyldaunomycinone 9 grams of anhydrous aluminum chloride were dissolved in 150 ml. of nitrobenzene, and a solution of 5 gms. of daunomycinone trimethyl ether(*) in 250 ml. of nitrobenzene was slowly added thereto at room temperature. After 2 hours, 500 ml. of petroleum ether were added and the resulting precipitate was collected, washed with 50 ml. of petroleum ether and added to 500 ml. of a 3% solution of oxalic acid.

\* Daunomycinone trimethyl ether was prepared according to the procedure described in Arcamone et al, Gazz. Chim. Ital., 100, 949 (1970).

The solution was then extracted with 300 ml. of chloroform and the chloroform extracts evaporated and chromatographed on a silica gel column using 2,000 ml. of chloroform as the solvent. The main fraction was collected and crystallized from 50 ml. of a 1:1 (vol.) ether-petroleum ether mixture to give 3 g. of 7-O-methyldaunomycinone, m.p. 183°–185°C., $[\alpha]_D^{20}$ + 150° (c = 0.1, dioxane). NMR (CDCl$_3$):2.41$\delta$ (s, 3H, CH$_3$CO); 3.62$\delta$ (s, 3H, CH$_3$O-C(7)); 4.07$\delta$ (s, 3H, CH$_3$O-C (4)), 12.86$\delta$ and 13.63$\delta$ (two singlets, 2H, C(6)OH and C(11)OH).

Variations and modifications can, of course, be made without departing from the spirit and scope of the invention.

Having thus described our invention, what we desire to secure by Letters Patent and hereby claim is:

1. A process for preparing an anthracycline derivative of the formula

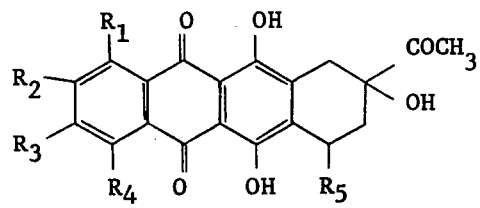

(I)

wherein R$_1$, R$_2$, R$_3$ and R$_4$ are independently selected from the group consisting of hydrogen, chlorine, bromine and methoxy group, with the proviso that at least one of R$_1$, R$_2$, R$_3$ and R$_4$ is methoxy; and wherein R$_5$ is selected from the group consisting of hydrogen, OH, OR and OCOR, in which R is an alkyl group of 1 to 4 carbon atoms; said process comprising reacting a compound of the formula

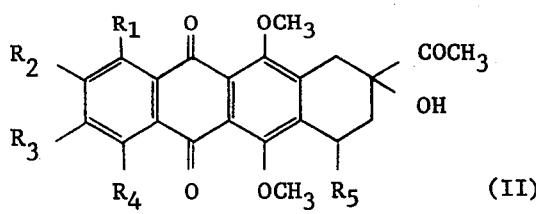

(II)

wherein R$_1$, R$_2$, R$_3$, R$_4$ and R$_5$ are as defined above with an aluminum halide in the presence of a solvent selected from the group consisting of chlorobenzene, bromobenzene, and nitrobenzene, at a temperature of from 0° to 50°C., and isolating the demethylated product from the reaction mixture.

2. A process according to claim 1, wherein the aluminum halide is aluminum chloride or aluminum bromide.

3. A process according to claim 1, wherein the solvent is nitrobenzene.

4. A process according to claim 1, wherein the temperature is not more than 20°C.

* * * * *